(12) United States Patent
Sorano et al.

(10) Patent No.: US 12,226,132 B2
(45) Date of Patent: Feb. 18, 2025

(54) GRANULE MADE OF BIOCOMPATIBLE METALLIC MATERIAL FOR VERTEBROPLASTY

(71) Applicant: MT ORTHO S.R.L., Aci Sant'antonio (IT)

(72) Inventors: Gaetano Sorano, Trecastagni (IT); Roberto Drago, Viagrande (IT)

(73) Assignee: MT ORTHO S.R.L., Aci Sant'Antonio (IT)

( * ) Notice: Subject to any disclaimer, the term of this patent is extended or adjusted under 35 U.S.C. 154(b) by 713 days.

(21) Appl. No.: 17/440,738

(22) PCT Filed: Mar. 6, 2020

(86) PCT No.: PCT/IB2020/051969
§ 371 (c)(1),
(2) Date: Sep. 17, 2021

(87) PCT Pub. No.: WO2020/188393
PCT Pub. Date: Sep. 24, 2020

(65) Prior Publication Data
US 2022/0183727 A1 Jun. 16, 2022

(30) Foreign Application Priority Data
Mar. 19, 2019 (IT) .................. 102019000003947

(51) Int. Cl.
*A61B 17/70* (2006.01)
*A61F 2/28* (2006.01)
(Continued)

(52) U.S. Cl.
CPC ...... *A61B 17/7095* (2013.01); *A61F 2/30942* (2013.01); *A61F 2/44* (2013.01);
(Continued)

(58) Field of Classification Search
CPC ............ A61B 17/7095; A61F 2/30965; A61F 2002/5055; A61F 2002/2835;
(Continued)

(56) References Cited

U.S. PATENT DOCUMENTS

| 2006/0085081 A1* | 4/2006 | Shadduck | A61B 17/68 |
| | | | 623/23.76 |
| 2013/0101673 A1 | 4/2013 | Borden | |
| 2017/0157287 A1* | 6/2017 | Francaviglia | B01J 19/121 |

FOREIGN PATENT DOCUMENTS

| EP | 3 169 375 | 5/2017 |
| WO | 2016/009406 | 1/2016 |
| WO | 2016/009406 A1 | 1/2016 |

OTHER PUBLICATIONS

International Search Report for PCT/IB2020/051969 dated Jun. 25, 2020, 3 pages.

(Continued)

*Primary Examiner* — Ricardo D Morales
(74) *Attorney, Agent, or Firm* — NIXON & VANDERHYE

(57) ABSTRACT

Disclosed is a granule made of biocompatible metallic material, in particular made of titanium or titanium alloys, for vertebroplasty operations. The granule has a spherical shape and includes a central core with a solid structure, also spherical, having an outer surface from which a first diametrical rib and a second diametrical rib also having a solid structure, protrude. The ribs are advantageously arranged according to two diameters orthogonal to each other. The granule also includes a portion having a trabeculated structure which extends between the outer surface of the central core and the outer surface of the granule itself.

20 Claims, 3 Drawing Sheets

(51) Int. Cl.
  *A61F 2/30*    (2006.01)
  *A61F 2/44*    (2006.01)
  *A61L 27/06*   (2006.01)
  *A61L 27/56*   (2006.01)
  *B33Y 10/00*   (2015.01)
  *B33Y 80/00*   (2015.01)

(52) U.S. Cl.
  CPC ............... *A61L 27/06* (2013.01); *A61L 27/56* (2013.01); *A61F 2002/2835* (2013.01); *A61F 2002/30011* (2013.01); *A61F 2002/30242* (2013.01); *A61F 2002/3092* (2013.01); *A61F 2002/3093* (2013.01); *A61F 2002/30985* (2013.01); *A61F 2310/00023* (2013.01); *A61L 2400/06* (2013.01); *A61L 2430/38* (2013.01); *B33Y 10/00* (2014.12); *B33Y 80/00* (2014.12)

(58) Field of Classification Search
  CPC .... A61F 2002/3006; A61F 2002/30062; A61F 2002/30108; A61F 2002/3011; A61F 2002/30112
  See application file for complete search history.

(56) References Cited

OTHER PUBLICATIONS

Written Opinion of the ISA for PCT/IB2020/051969 dated Jun. 25, 2020, 5 pages.

\* cited by examiner

GRANULE MADE OF BIOCOMPATIBLE METALLIC MATERIAL FOR VERTEBROPLASTY

BACKGROUND OF THE INVENTION

Field of the Invention

The present invention relates to a specific configuration of a granule made of biocompatible metallic material, in particular made of titanium or its alloys, to be used in vertebroplasty or transcutaneous kyphoplasty surgery.

Vertebroplasty, or kyphoplasty, is a treatment used in patients suffering from vertebral compression fractures.

Description of the Related Art

The present applicant is the owner of granted Italian patent nr. 0001425055, and pending European patent application EP 3169375, claiming the priority of said Italian patent, which describe granules in biocompatible material suitable for use in vertebroplasty surgery.

Said prior patent of the same Applicant therefore proposes a prosthetic device in biocompatible material, in particular in titanium or its alloys, in the form of granules comprising at least an outer surface portion having a porosity suitable for allowing osseointegration and favouring bone growth.

This solution offers an innovative alternative to systems known by the state of the art, which provided for the use of bone cement such as PMMA (polymethylmethacrylate).

The most widely-used technique involves the use of a balloon: after having practiced the necessary access route, the surgeon inserts a cannula in the collapsed vertebra, that allows the insertion of the balloon inside the main body of the vertebra, in the area in which the collapsed cancellous bone no longer exerts its supporting function.

With the patient in a prone and distracted position, the cannula with transpeduncular access is inserted directly into the main body of the vertebra.

The whole operating phase takes place under endoscopy.

Once the correct position has been reached inside the main body of the vertebra, a bone-compression device is inserted by means of a cannula, which is nothing more than a balloon which is inflated by means of liquid or equivalent systems.

The balloon exerts the function of compacting the trabeculae of the cancellous bone of the main body of the vertebra, while expanding the internal cavity of the collapsed vertebra.

Once the cavity of the vertebra has been expanded by means of the balloon, the latter is retracted and cement of common use in orthopedics, as already mentioned PMMA (polymethylmethacrylate), is inserted in the cavity thus obtained, again by means of a cannula.

The use of cement in kyphoplasty has the advantage of immediately guaranteeing primary stability, i.e. resistance to compression loads acting on the column, which guarantees a very short hospital stay for the patient, so much so that the patient himself can be discharged within a few days after surgery.

The drawbacks that negatively affect the traditional techniques which provide for the use of bone cement, have been overcome by the applicant through the use of granules in biocompatible material for vertebroplasty operations, according to the teachings of EP3169375.

Within these teachings, the present Applicant has developed a specific and preferred configuration of the granule in biocompatible metallic material, such as titanium or its alloys, for vertebroplasty, of which a detailed description is provided hereunder.

SUMMARY OF THE INVENTION

The main task of the present invention is to provide a granule in biocompatible metallic material, such as titanium or its alloys, which is optimized for use in vertebroplasty operations.

Within this task, the objective of the present invention is therefore to provide a granule in biocompatible metallic material, such as titanium or its alloys, for vertebroplasty which provides optimal primary stability, i.e. resistance to compressive loads acting on the optimized column, and which at the same time allows an optimized osseointegration and osteoinductive capacity.

A further objective of the present invention is to provide a granule in biocompatible metallic material for vertebroplasty that can be introduced into the damaged vertebra by means of the same cannula adopted by the surgeon for inserting the balloon used for compacting the trabeculae of the cancellous bone of the main body of the vertebra, at the same time expanding the internal cavity of the collapsed vertebra, according to the traditional surgical technique.

Furthermore, an objective of the present invention is to provide a granule in biocompatible metallic material for vertebroplasty which, due to its geometry, has an elasticity as close as possible to the average elasticity of the reference bone of the vertebra to be restored and whose growth must be stimulated and osseointegration obtained.

This task and these and other objectives according to the present invention are achieved by a granule in biocompatible metallic material for vertebroplasty as disclosed.

Further characteristics of the granule in biocompatible metallic material for vertebroplasty according to the present invention are also disclosed.

BRIEF DESCRIPTION OF THE DRAWINGS

The characteristics and the advantages of the granule in biocompatible metallic material for vertebroplasty according to the present invention will appear more evident from the following detailed description, provided by way of non-limiting example, referring to the attached schematic drawings in which.

DESCRIPTION OF THE PREFERRED EMBODIMENTS

Figure 2:
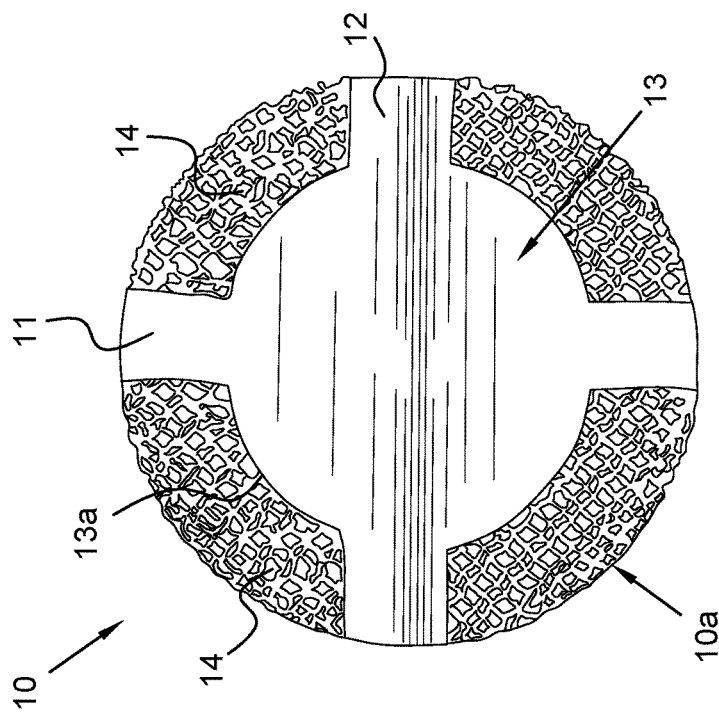
FIG. 2 shows a section of the granule of FIG. 1.

According to the present invention, granules in biocompatible metallic material, more particularly based on titanium and/or its alloys, are produced with such characteristics as to enable, at the same time, their insertion in the operative phase inside the main body of the vertebra, resistance to primary loads, osseointegration of the granules over time and stimulation of bone regrowth.

The granules 10 according to the present invention preferably have a spherical shape, with a maximum external diameter of less than 4 mm, more preferably with an external diameter of 3.3 mm, and have a substantially spherical central core 13, from which a first diametrical rib 11 and a second diametrical rib 12, arranged according to two diameters orthogonal to each other, protrude and extend.

Said first 11 and second 12 diametrical ribs preferably have a solid structure made of biocompatible metallic material, preferably titanium or its alloys, of which the granule 10 is composed.

These solid ribs 11, 12 therefore have the appearance of diametrical beams orthogonal to each other, which have continuity of material with the central core 13, also having a solid structure.

Figure 1:
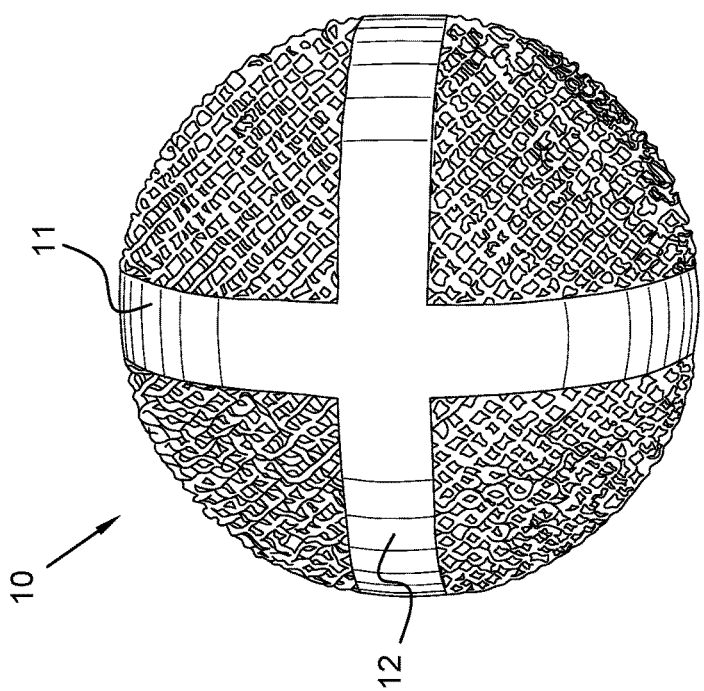
FIG. 1 shows an overall perspective view of the granule in biocompatible metallic material according to the present invention.
Figure 3:
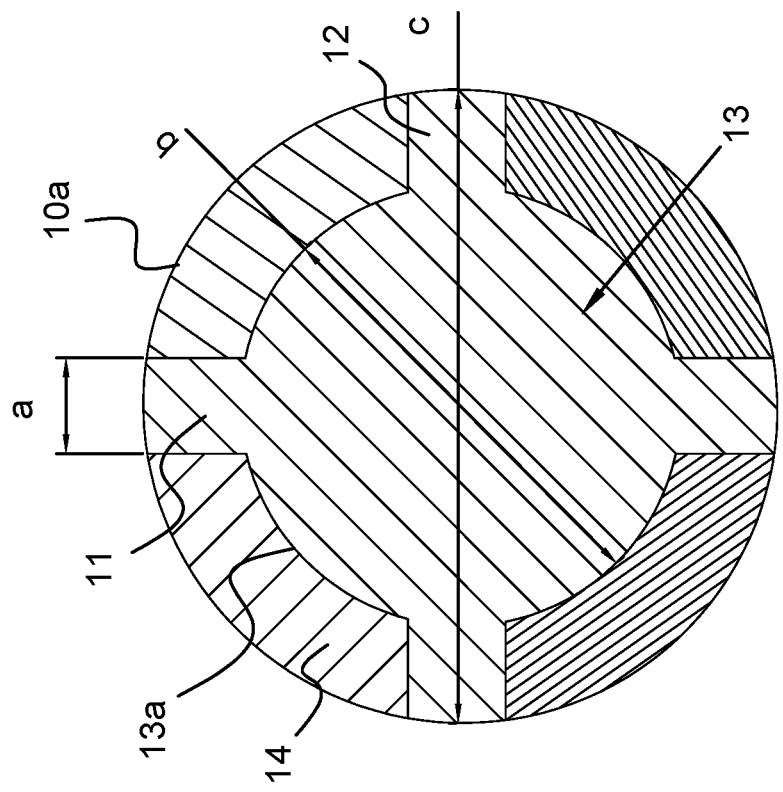
FIG. 3 shows a schematic representation of the same sectional view of FIG. 2.

According to what can be seen for example in the attached figures, and in particular in the section of FIG. 1, the granule 10 according to the present invention further comprises an area having a trabeculated structure 14 which affects the portion of said granule 10 extending from the outer surface 10a of the granule itself as far as the outer surface 13a of said central core 13, according to what can be seen for example in FIGS. 2 and 3.

In particular in FIG. 3, which shows a schematic view of the granule 10 according to the present invention in cross section with a diametrical plane, the reference number 14 indicates the area having a trabeculated structure, the remaining part of the granule, that is the central nucleus 13 from which the diametrical ribs 11 and 12 extend, having a solid structure.

Again with reference to FIG. 3, the letters a, b and c respectively indicate the width of the ribs 11 and 12, which preferably measures 0.5 mm, the internal diameter of the central core 13, preferably equal to 2.5 mm, and the external diameter of the granule 10, preferably equal to 3.3 mm.

The granules 10 according to the present invention are advantageously produced by means of production techniques which provide for the localized microcasting of powders (metallic or polymeric) by means of high-energy electron beams.

These techniques, known as EBM (Electron Beam Melting), are currently extremely advanced manufacturing technologies that allow objects to be created with a very complex geometry and with a different surface roughness starting from a computer design of the finished product, which is processed by computerized machines that guide the electron beam in its action.

Electron-beam fusion is a relatively new rapid prototyping technique for the production of implant structures, and allows the production of complex three-dimensional geometries.

Using this technique, the present Applicant has developed the granule 10 object of the present invention in which the part having a regular trabecular structure has a pore size between one trabecula and the other in the order of a hundred microns.

More particularly, the regular trabecular structure has a pore diameter ranging from 400 to 800 microns, even more preferably the pore diameter is about 600 microns, preferably 640 microns.

The trabecular structure in titanium or titanium alloys, in particular, thanks to an elastic modulus which is very close to that of the natural trabecular bone, restores the physiological transfer of loads, avoiding damage to the bone and actually promoting its regrowth.

Returning to the specific configuration of the granule 10 according to the present invention, the area having a trabeculated structure 14 which involves at least a portion of said granule 10 which extends from the outer surface of the granule itself to said central core 13, advantageously has a trabeculated structure produced through an EBM production process that uses the known type of software element called "dode-thin".

Figure 4:
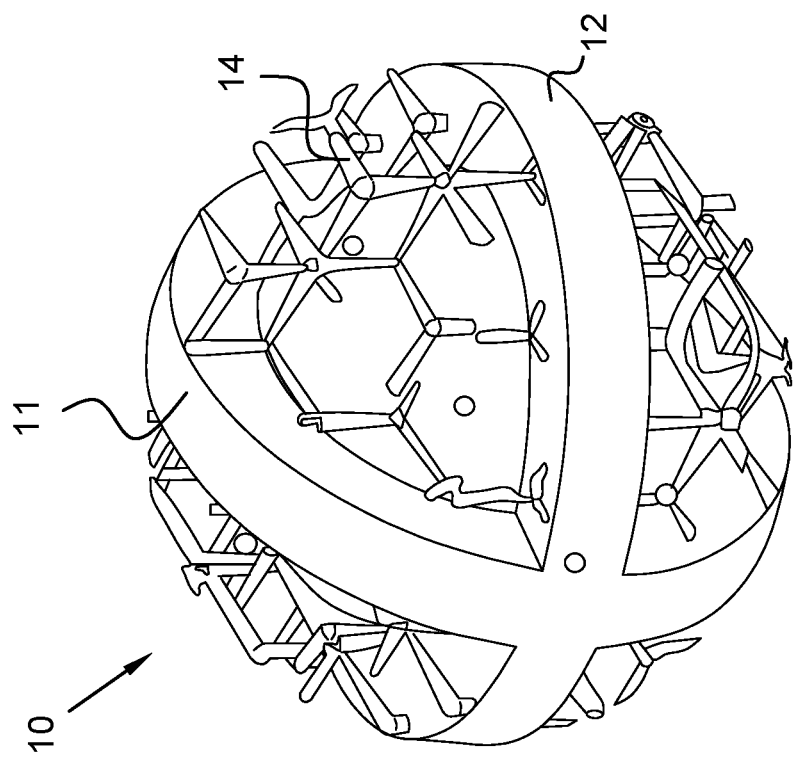
FIG. 4 shows a schematic perspective view representing the dode-thin structure of the trabeculated part of the granule according to the present invention.
Figure 5A:
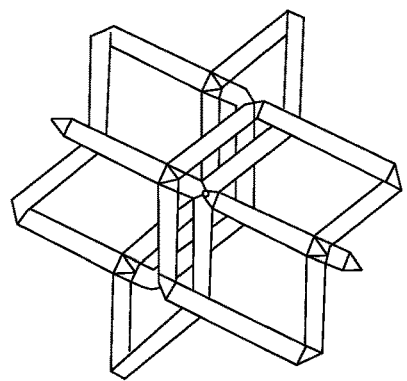
FIGS. 5A and 5B and FIGS. 6A and 6B show the known dode-thin structure of the trabeculation of the granule according to the present invention.
Figure 6A:
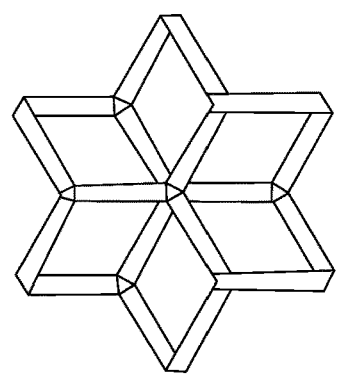
Figure 5B:
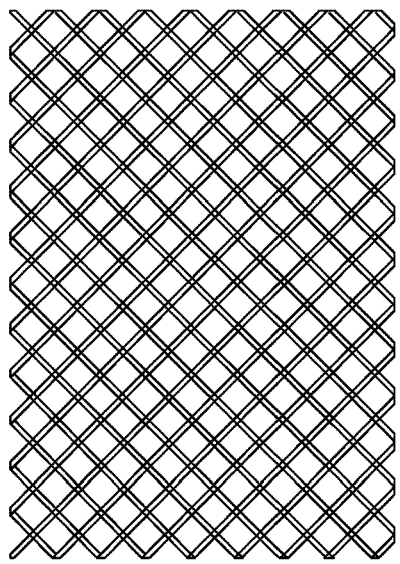
Figure 6B:
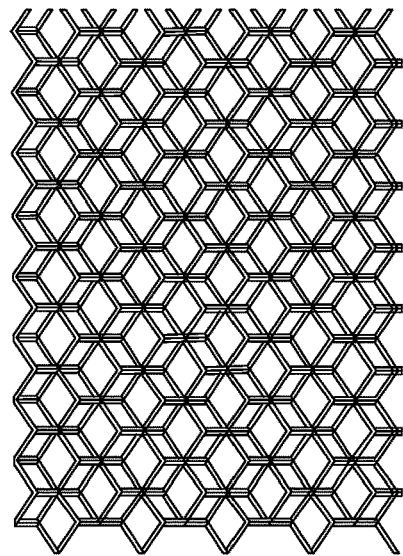

With particular reference to FIG. 4, this schematically shows a phase of the software implementation of the "dode-thin"-type mesh, whereas FIG. 5A shows the orientation of the "dode-thin" element corresponding to the hexahedral geometry shown in FIG. 5B, which is in correspondence with the faces of the three-dimensional trabecular structure, and FIG. 6A shows the orientation of the "dode-thin" element corresponding to the octahedral geometry shown in FIG. 6B which is in correspondence with the diagonals (at 45°) of the three-dimensional trabeculated structure.

CAD-CAM software implements the mesh according to the known "dode-thin" elements, starting from a design showing a level of detail as illustrated for example in FIG. 4, finally reaching a product, produced using EBM techniques, as shown in FIGS. 1 and 2.

The Applicant has also verified that the particular configuration of the granule 10 according to the present invention, and in particular the presence of a solid central core 13 from which diametrical ribs 11, 12, also solid, extend, and the large trabeculated area 14 which extends from the outer surface 13a of the central core 13 to the outer 10a of the granule 10, allows a mechanical behaviour to be obtained in in-vivo implantation, which allows loads to be supported, immediately obtaining the primary stability of the implant.

From the description provided so far, the characteristics of the granule in biocompatible metallic material, particularly in titanium or its alloys, for use in vertebroplasty operations, are evident, as also the relative advantages.

It is understood that the granule for vertebroplasty operations thus conceived can undergo modifications and/or variations, all of which fall within the scope of the invention, whose protection scope is defined by the enclosed claims.

In particular, the materials described, as also the dimensions, can vary according to requirements.

The invention claimed is:

1. A granule made of biocompatible metallic material for vertebroplasty operations, wherein the granule has a spherical shape and comprises a central core with a solid structure, also spherical, having an outer surface from which a first diametrical rib and a second diametrical rib also having a solid structure, protrude, arranged according to two diameters orthogonal to each other, the granule comprising a portion having a trabeculated structure which extends between the outer surface of said central core and the outer surface of the granule itself.

2. The granule according to claim 1, wherein said first diametrical rib and said second diametrical rib extend from said central core to the outer surface of said granule.

3. The granule according to claim 1, wherein the external diameter of said granule is equal to 3.3 mm and that the diameter of the central core is equal to 2.5 mm.

4. The granule according to claim 1, wherein each of said first and second ribs have a width equal to 0.5 mm.

5. The granule according to claim 1, wherein the granule is produced by means of EBM rapid prototyping techniques.

6. The granule according to claim 1, wherein said portion having a trabeculated structure has an average pore size ranging from 400 to 800 microns.

7. The granule according to claim 1, wherein said portion having a trabeculated structure has a trabeculation produced by the EBM technique composed of dode-thin elements.

8. The granule according to claim 2, wherein the external diameter of said granule is equal to 3.3 mm and that the diameter of the central core is equal to 2.5 mm.

9. The granule according to claim 2, wherein each of said first and second ribs have a width equal to 0.5 mm.

10. The granule according to claim 3, wherein each of said first and second ribs have a width equal to 0.5 mm.

11. The granule according to claim 2, wherein the granule is produced by means of EBM rapid prototyping techniques.

12. The granule according to claim 3, wherein the granule is produced by means of EBM rapid prototyping techniques.

13. The granule according to claim 4, wherein the granule is produced by means of EBM rapid prototyping techniques.

14. The granule according to claim 2, wherein said portion having a trabeculated structure has an average pore size ranging from 400 to 800 microns.

15. The granule according to claim 3, wherein said portion having a trabeculated structure has an average pore size ranging from 400 to 800 microns.

16. The granule according to claim 4, wherein said portion having a trabeculated structure has an average pore size ranging from 400 to 800 microns.

17. The granule according to claim 5, wherein said portion having a trabeculated structure has an average pore size ranging from 400 to 800 microns.

18. The granule according to claim 2, wherein said portion having a trabeculated structure has a trabeculation produced by the EBM technique composed of dode-thin elements.

19. The granule according to claim 3, wherein said portion having a trabeculated structure has a trabeculation produced by the EBM technique composed of dode-thin elements.

20. The granule according to claim 4, wherein said portion having a trabeculated structure has a trabeculation produced by the EBM technique composed of dode-thin elements.

* * * * *